United States Patent [19]

Creeth et al.

[11] Patent Number: 5,560,517
[45] Date of Patent: Oct. 1, 1996

[54] TOOTHPASTE COMPOSITION

[75] Inventors: Jonathan E. Creeth, Cheshire; Paul I. Riley, Wirral; Mark E. Laing, Cheshire, all of United Kingdom

[73] Assignee: Chesebrough-Pond's USA Co., Division of Conopco, Inc., Greenwich, Conn.

[21] Appl. No.: 262,196

[22] Filed: Jun. 20, 1994

Related U.S. Application Data

[62] Division of Ser. No. 966,212, Oct. 26, 1992, Pat. No. 5,348,732.

[30] Foreign Application Priority Data

Oct. 29, 1991 [GB] United Kingdom ............ 9122909

[51] Int. Cl.$^6$ .................... B65D 35/02; A61K 7/16
[52] U.S. Cl. .................... 222/92; 222/107; 424/49
[58] Field of Search ................ 222/92, 94, 107; 424/49–58; 53/475

[56] References Cited

U.S. PATENT DOCUMENTS

| | | | |
|---|---|---|---|
| 2,470,906 | 5/1949 | Taylor | 167/93 |
| 3,925,543 | 12/1975 | Donohue | 424/52 |
| 4,211,341 | 7/1980 | Weyn . | |
| 4,317,742 | 3/1982 | Yamaji et al. | 252/188 |
| 4,335,102 | 6/1982 | Nakashima et al. | 424/52 |
| 4,363,794 | 12/1982 | Ochiai et al. | 424/52 |
| 4,391,368 | 7/1983 | Washington, Jr. | 222/107 |
| 4,487,757 | 12/1984 | Kiozpeoplou . | |
| 4,798,311 | 1/1989 | Workum | 222/131 |
| 4,842,165 | 6/1989 | Van Coney | 222/95 |
| 4,997,640 | 3/1991 | Bird et al. | 424/52 |
| 5,094,842 | 3/1992 | Riley | 424/52 |
| 5,096,702 | 3/1992 | Rolla et al. | 424/52 |
| 5,188,820 | 2/1993 | Cummins et al. | 424/49 |
| 5,188,822 | 2/1993 | Viccaro et al. | 424/52 |
| 5,217,050 | 6/1993 | Varlet | 53/510 |
| 5,258,173 | 11/1993 | Waterfield | 424/49 |

FOREIGN PATENT DOCUMENTS

| | | |
|---|---|---|
| 0076563 | 4/1983 | European Pat. Off. . |
| 0243321 | 10/1987 | European Pat. Off. . |
| 0251661 | 1/1988 | European Pat. Off. . |
| 642692 | 1/1948 | United Kingdom . |
| 1534881 | 12/1978 | United Kingdom . |
| 1561418 | 2/1980 | United Kingdom . |
| 2112642 | 7/1983 | United Kingdom . |

OTHER PUBLICATIONS

EP Search Report–EP 92 30 9820.
Wellcome Foundation Ltd.–Abstract Oct. 28, 1948.

*Primary Examiner*—Kevin P. Shaver
*Attorney, Agent, or Firm*—Milton L. Honig

[57] ABSTRACT

Packaged toothpaste formulations which contain air sensitive components, e.g. vitamin C, are prevented from discoloring or otherwise degrading, by placing adjacent to an area of the packaging which may allow air access to the formulation, e.g. an air permeable collar, a nozzle, or the wall of an air permeable tube, a body (e.g. plug or layer) of material which does not contain any air sensitive components. Preferably, the latter body of material is the packaged toothpaste but without the air sensitive components.

8 Claims, No Drawings

5,560,517

1
TOOTHPASTE COMPOSITION

CROSS REFERENCES

This is a Divisional application of Ser. No. 07/966,212 filed Oct. 26, 1992, which matured into U.S. Pat. No. 5,348,732.

FIELD OF THE INVENTION

This invention relates to toothpaste compositions which contain air sensitive molecules which show a tendency to degrade upon exposure to air, leading to deleterious effects such as discolouration, loss or spoiling of flavour or the like. The invention also relates to methods for the prevention of such air-induced degradation.

BACKGROUND OF THE INVENTION

It is frequently desirable to incorporate into toothpaste formulations certain molecules which may often be air sensitive, for example vitamin C. Often the degradation products produced on exposure of the toothpaste formulation to air are a different colour to the original compound; in the case of vitamin C its air decomposition products are coloured brown. Hence it has been a major disincentive to manufacturers who would wish to incorporate such air sensitive compounds in toothpaste formulations that such pastes tend to discolour after a period of time, thereby appearing visually unattractive to a potential user. Similar problems may occur with other air sensitive substances such as certain flavour molecules or pharmaceuticals, which upon air-induced degradation result in impairment or even loss of the respective desired properties of the toothpaste.

Such problems have been partially overcome by the use of air impermeable tubes. Traditional tubes such as those made from metals such as aluminium are regarded by consumers as old fashioned, and also these tubes are not ideal from other perspectives, as they tend to crack after extended use, thereby causing the toothpaste to leak. Paint on the surfaces of these tubes also tends to crack and flake off upon extended use.

Plastics tubes now enjoy popularity. However, these also have disadvantages, since they are prone to the permeation of air through the tube and into the contents, and also the permeation of volatile substances in the paste out of the tube, with the result that the toothpaste shows a tendency to discolour and/or lose flavour or other active properties on storage. Air impermeable plastics tubes have been developed to overcome these problems, and have in general been successful in preventing air gaining access to the toothpaste. Such solutions to these problems are not without their own problems though; an air impermeable tube costs typically 3–10 times the amount of an ordinary plastic tube.

Laminated tubes, for example tubes containing a metal layer such as aluminium laminated between two layers of a plastics material such as polyethylene, have also been developed which in practice have most of the advantages of both plastic and metal tubes. Such tubes are effectively air impermeable, and are the generally preferred choice of manufacturers in which to pack toothpaste for commercial sale.

However, because of technical problems associated with the assembly of such tubes, complete tubes made entirely of laminated material have not been available. In practice, sleeves of laminated tube material are heat sealed to a preformed plastics collar nozzle assembly which is sealed by a plastics cap. Toothpaste is then dosed into the other open end, which is then crimped or otherwise sealed.

The toothpaste can then be dispensed through the preformed nozzle.

Overall it has not been possible to totally prevent toothpaste contained in tubes from coming into contact with air. Where this is caused by the ingress of air on prolonged storage, it is observed that most of this ingress occurs through the collar of the tube; the toothpaste is also exposed to the small amount of air that typically remains in the nozzle area of the tube after it has been filled. The problem is exaggerated if the filling of the tube does not occur uniformly, as is bound to happen occasionally in the mass manufacture of packaged toothpaste. In such circumstances, small unwanted air voids will be trapped in the toothpaste, usually adjacent the collar/nozzle assembly, after filling. This is still a general problem for toothpaste manufacturers since it can lead to dehydration, discolouration and flavour loss from the paste, in particular in parts of the tube near the collar. The problem is particularly acute for the manufacturer of toothpaste who wishes to include air sensitive compounds in a toothpaste formulation, such as for example vitamin C. It is found that after storage such vitamin C containing toothpaste formulations discolour in the vicinity of the tube collar; hence the first few centimeters of the toothpaste that are dispensed are discoloured. Such a product is obviously off-putting to the consumer, if for example the bulk of the toothpaste is coloured white but the first few centimeters are coloured brown.

It has also been observed that even if formulations containing air sensitive compounds such as vitamin C are stored in special tubes which have been made air impermeable, the surface of the paste which is in contact with the air contained in the aforementioned nozzle gap rapidly turns brown. Hence, even the provision of totally air impermeable tubes would not totally solve the problem, whilst using current technology the most cost effective toothpaste packaging is not totally air impermeable.

Hence there exists a need for a method of packaging toothpaste which contains air sensitive components which prevents the discolouration or other form of degradation of such toothpaste caused by exposure of areas of the toothpaste to air. The problem is noticeable even when air impermeable packaging is used, but is particularly noticeable when the packaging used is not totally air impermeable, for example if an effectively air impermeable laminated toothpaste tube is fitted with an air permeable (e.g. polyethylene) collar.

It is known in the art to provide different reactive components of a toothpaste composition which are to be reacted together in use in separate compartments of a toothpaste package, which two components are brought into contact with each other for reaction together at the time of dispensation from the package. Examples of such known systems are described in GB-A-1561418 and GB-A-2112642. These systems however do not address the problem of air-induced degradation of either of the reactive components, or indeed other components of the toothpaste composition.

SUMMARY OF THE INVENTION

We have surprisingly found that a solution to the problem of degradation of toothpaste formulations which contain one or more air sensitive compounds is to place, when filling the tube and adjacent to the area or areas of the tube through which air may gain access, a body of material which does not contain any air sensitive compounds. The air-sensitive compound-free body of material may for example be in the form of a plug or lining layer, or even a combination of the two.

DETAILED DESCRIPTION OF PREFERRED EMBODIMENTS

In a preferred solution, the body of material which does not contain any air sensitive compounds is another toothpaste formulation, preferably a plug or layer of toothpaste formulation which is identical to the first toothpaste formulation except that it does not contain the air sensitive compound or compounds.

The invention also provides a packaged toothpaste formulation comprising a toothpaste tube, a toothpaste composition containing one or more air sensitive compounds, and a toothpaste composition not containing any air sensitive compounds.

In a preferred embodiment, the toothpaste composition not containing air sensitive compounds is located in a toothpaste tube adjacent to the parts of the package which may either trap air or allow the ingress of air, and the toothpaste composition containing the air sensitive compound(s).

In the case of toothpaste formulations which contain vitamin C for example, this means placing a layer of the same toothpaste formulation but which does not contain vitamin C adjacent to any areas of the packaging through which air may gain access. This may be for example adjacent to the collar of the tube if a tube is used which has an air impermeable laminated body and an air permeable collar, and/or adjacent to the nozzle area of the tube where an air gap may exist after filling. Additionally or alternatively, it may include coating substantially the whole internal area of an otherwise empty air permeable toothpaste tube with the same toothpaste formulation but which does not contain any air sensitive compounds, if the body of the toothpaste is to contain the air sensitive compound(s).

In a preferred embodiment of the invention, in particular where the toothpaste not containing air sensitive compounds is a plug adjacent to the collar of the tube, the toothpaste not containing air sensitive compounds comprises 1–20% of the total amount of the toothpaste formulation, more preferably 4–13% of the total amount of the toothpaste formulation.

Toothpastes made according to the method of the invention have proved remarkably resistant to degradation by air on storage. This invention is all the more surprising since if the body of material not containing the air sensitive component adjacent to the air permeable packaging element is an identical toothpaste formulation, except that it does not contain the air sensitive component, and degradation is detected for example by discolouration, one would expect some degree of discolouration to occur in the layer not containing the air sensitive component since many air sensitive components are mobile in the toothpaste formulation matrix. Therefore, one would expect the air sensitive components to spread into the part of the formulation not containing them (i.e. adjacent to the air permeable packaging) and cause some discolouration there, but this has been observed only to occur at a very slow rate.

When used in conjunction with preferred toothpaste tubes which, as has been previously explained, comprise a laminated body and an air permeable collar, the invention provides an extremely convenient and cost effective way of packaging toothpastes the bulk of which contain one or more air sensitive materials.

The part of the toothpaste formulation not containing air sensitive compounds can in a preferred embodiment also act as a matrix in which oxygen scavenger compounds, such as stannous compounds or sodium metabisulphite, may be contained. This further increases the plug's or layer's effectiveness in preventing degradation.

A preferred method of manufacture of packaged toothpaste according to the invention is to provide a laminated tube body with an air permeable collar already sealed to it by conventional techniques, positioned such that the unsealed tube end is located vertically above the air permeable collar. The toothpaste composition not containing air sensitive compounds can then be dosed into the tube, followed by the bulk of the toothpaste which does contain air sensitive compound(s). The open end of the tube can then be crimped or otherwise sealed by conventional techniques.

When used in combination with other methods of preventing air ingress into toothpaste formulations, such as for example utilising totally air impermeable packaging, the method of the invention can provide a particularly effective way of preventing the degradation of air sensitive compounds in toothpastes.

The present invention may be used to prevent or inhibit air-induced degradation in packaged toothpaste of a variety of substances which impart desirable properties, yet which tend to result in deleterious effects such as discolouration, loss of colour, loss or impairment of flavour or pharmaceutical activity, when subjected to prolonged exposure to air, especially at relatively high storage temperatures.

In addition to vitamins such as vitamin C, other substances to which the invention may be usefully applied include for example the following:

other ene-diols (vitamin C is an example of such a compound)

catechois tannins metal salts in low oxidation states which change colour on air-oxidation, e.g. ferrous salts iodide salts flavour molecules which are susceptible to loss of or change in flavour upon air-oxidation.

The invention will now be illustrated with reference to the following examples.

EXAMPLE 1

The following basic toothpaste formulation was prepared:

| Component | % w/w |
| --- | --- |
| Silica | 18.5 |
| Sorbitol (70% solution) | 45.0 |
| Polyethylene glycol | 5.0 |
| Flavour | 1.4 |
| Binder | 0.9 |
| Whitener | 1.0 |
| Sodium fluoride | 0.22 |
| Sodium lauryl sulphate | 1.875 |
| Water | to 100 |

For the purpose of the comparative storage test, to the basic formulation was added vitamin C and stannous pyrophosphate (which can act as both an oxygen scavenger and a stabilizing agent for vitamin C). A further suitable oxygen scavenger is sodium metabisulphite.

| Formulation | | Weight % | |
|---|---|---|---|
| | | Plug | "Body" toothpaste formulation |
| I | stabilizing agent | 0 | 0 |
| | vitamin C | 0 | 0.25 |
| II | stabilizing agent | 1 | 1 |
| | vitamin C | 0 | 0.25 |
| III | stabilizing agent | 1 | 0 |
| | vitamin C | 0 | 0.25 |

All the figures are % w/w of the formulation. Each tube was dosed with 75 g of toothpaste formulation in total, of which the plug (if present) comprised 7.5 g. The formulations were dosed into laminated tubes, with the plug (if present) adjacent the collar part of the tube, and sealed by conventional techniques. The tubes were then subjected to elevated temperature storage tests at 37° C. and 50° C. to simulate longer term storage conditions. After periods of 5 weeks and 3 months, the samples were inspected for browning both by squeezing out a ribbon of paste, and also by cutting open the tube and viewing the contents.

The discolouration of the pastes in the tubes was assessed according to the following scale:

| Grade | Description |
|---|---|
| 0 | No colour change |
| 1 | Detectable colour change, not noticeable in normal use |
| 2 | Detectable colour change, may be noticeable in normal use |
| 3 | Detectable colour change, clearly visible, no browning |
| 4 | Mild browning |

Results

| | | | Colourchange | | | |
|---|---|---|---|---|---|---|
| | | | 5 weeks | | 3 months | |
| Temperature | Formulation | Plug | Neck | Body | Neck | Body |
| 50° C. | I | No | 3 | 0 | 3 | 1 |
| | | Yes | 0 | 0 | 1 | 1 |
| | II | No | 0 | 0 | 2 | 0 |
| | | Yes | 0 | 0 | 1 | 0 |
| | III | No | 0 | 0 | 4 | 0 |
| | | Yes | 0 | 0 | 2 | 0 |
| 37° C. | I | No | 2 | 0 | 3 | 1 |
| | | Yes | 0 | 0 | 2 | 1 |
| | II | No | 0 | 0 | 1 | 0 |
| | | Yes | 0 | 0 | 0 | 0 |
| | III | No | 0 | 0 | 3 | 0 |
| | | Yes | 0 | 0 | 0 | 0 |

These results clearly show that discolouration of toothpaste formulations in parts of the tube where air may permeate or be otherwise present is improved (both in stabilized and unstabilized formulations) if a plug is used which does not contain the air sensitive compounds found in the body of the paste.

We claim:

1. A packaged toothpaste formulation comprising a toothpaste tube with an air permeable collar, a toothpaste composition comprising at least one air sensitive component, and a separate toothpaste composition which does not contain air sensitive components, wherein a plug or layer of the separate toothpaste composition not containing air sensitive components is situated adjacent the collar.

2. A packaged toothpaste formulation according to claim 1, wherein the toothpaste composition not containing air sensitive components is located in the toothpaste tube adjacent to parts of the toothpaste tube which may either trap air or allow the ingress of air, and the toothpaste composition containing the air sensitive component or components.

3. A packaged toothpaste formulation according to claim 1, wherein the separate toothpaste composition which does not contain air sensitive components is a coating on substantially the whole internal wall of the tube.

4. A packaged toothpaste formulation according to claim 1, wherein the tube includes a nozzle via which the toothpaste formulation is dispensed and the separate toothpaste composition which does not contain air sensitive components is situated adjacent to the nozzle.

5. A packaged toothpaste formulation according to claim 1, wherein the toothpaste composition not containing air sensitive components comprises 1–20% of the total amount of toothpaste in the package.

6. A packaged toothpaste formulation according to claim 1, wherein the toothpaste composition not containing air sensitive components additionally comprises an oxygen scavenging compound.

7. A packaged toothpaste formulation according to claim 1, wherein the air sensitive component is selected from the group consisting of: ene-diols; vitamins; catechols; tannins; metal salts in low oxidation states which change colour on air-oxidation; iodide salts; flavour molecules which are susceptible to loss of or change in flavour upon air-oxidation; and mixtures thereof.

8. A packaged toothpaste formulation according to claim 7, wherein the air sensitive component is vitamin C.

* * * * *